(12) United States Patent
Korchev et al.

(10) Patent No.: US 7,057,171 B2
(45) Date of Patent: Jun. 6, 2006

(54) PATCH-CLAMPING AND ITS USE IN ANALYZING SUBCELLULAR FEATURES

(75) Inventors: Yuri Evgenievich Korchev, London (GB); Max Joseph Lab, London (GB)

(73) Assignee: Imperial College Innovations Limited (GB)

( * ) Notice: Subject to any disclaimer, the term of this patent is extended or adjusted under 35 U.S.C. 154(b) by 0 days.

(21) Appl. No.: 10/472,427

(22) PCT Filed: Mar. 22, 2002

(86) PCT No.: PCT/GB02/01382

§ 371 (c)(1),
(2), (4) Date: Mar. 15, 2004

(87) PCT Pub. No.: WO02/077627

PCT Pub. Date: Oct. 3, 2002

(65) Prior Publication Data

US 2004/0140427 A1  Jul. 22, 2004

(30) Foreign Application Priority Data

Mar. 22, 2001 (GB) ................................. 0107231.3

(51) Int. Cl.
*G01N 23/00* (2006.01)
(52) U.S. Cl. ...................................... 250/306; 250/307
(58) Field of Classification Search ................ 250/306, 250/307, 309; 73/105
See application file for complete search history.

(56) References Cited

U.S. PATENT DOCUMENTS

| 4,924,091 A | * | 5/1990 | Hansma et al. ............. 250/306 |
| 6,048,722 A | | 4/2000 | Farb et al. |
| 6,929,934 B1 | * | 8/2005 | Korchev et al. ......... 435/173.1 |

FOREIGN PATENT DOCUMENTS

| EP | 0 697 111 B1 | 7/1997 |
| JP | 09196936 A | 7/1997 |
| JP | 09211010 | 8/1997 |
| JP | 09211010 A | 8/1997 |
| WO | WO 97 17426 A1 | 5/1997 |
| WO | WO 00 34776 A1 | 6/2000 |
| WO | WO 00 63736 A2 | 10/2000 |

OTHER PUBLICATIONS

Korchev, Y.E., et al. "Specialized scanning ion-conductance microscope for imaging of living cells," *J. Microscopy*, 1997, pp. 17-23, vol. 188, No. 1.
Korchev, Y.E., et al. "Scanning ion conductance microscopy of living cells," *Biophys. J.*, 1997, pp. 653-658, vol. 73, No. 1.

* cited by examiner

*Primary Examiner*—Kiet T. Nguyen
(74) *Attorney, Agent, or Firm*—Saliwanchik, Lloyd & Saliwanchik

(57) ABSTRACT

The present invention pertains to a method for investigating a cell, comprising bringing a probe close to the surface of the cell or part thereof, at a controlled distance therefrom; and into contact with the surface, essentially normal to the surface, to achieve patch-clamping.

15 Claims, 5 Drawing Sheets

Figure 1:
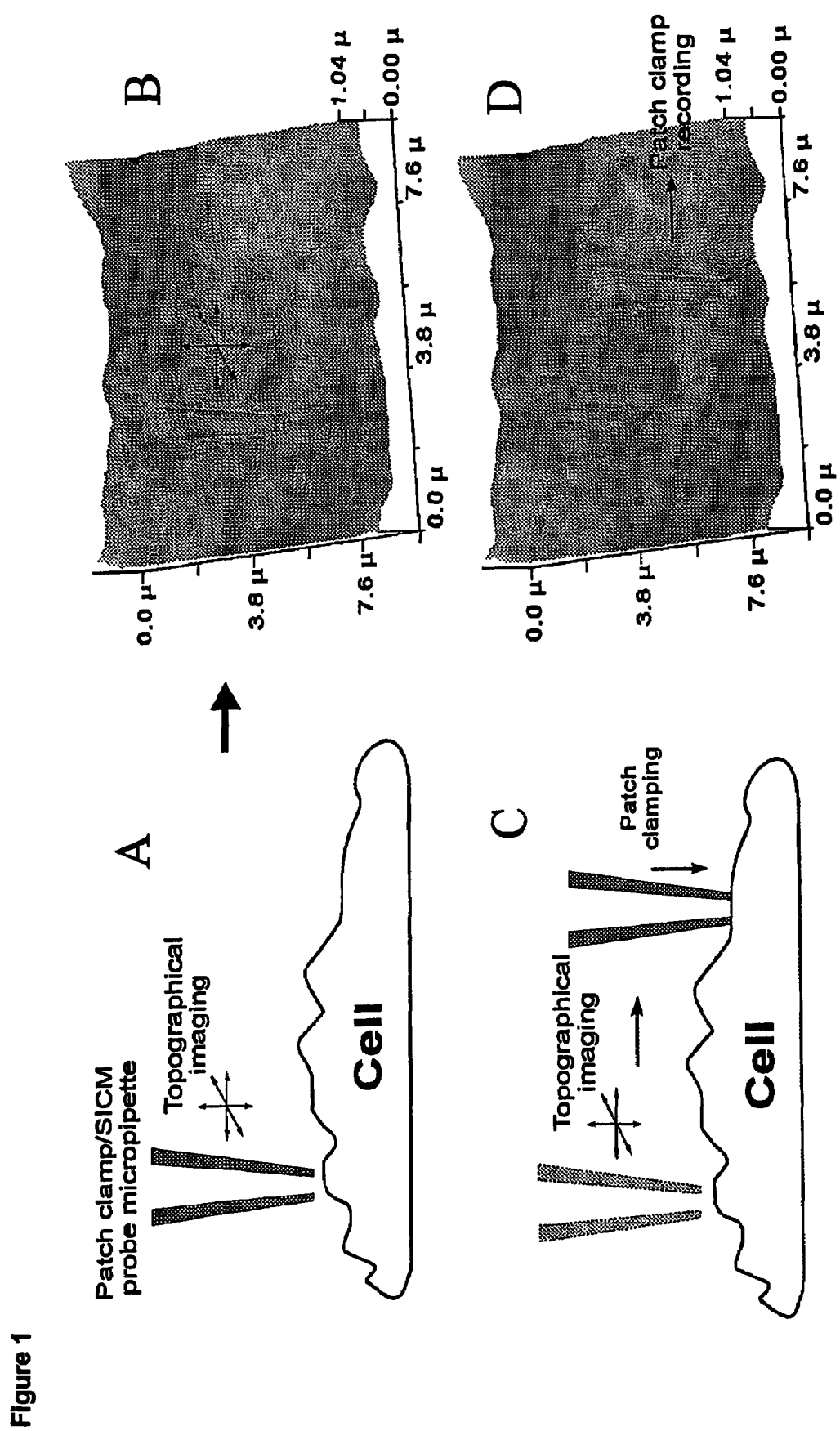

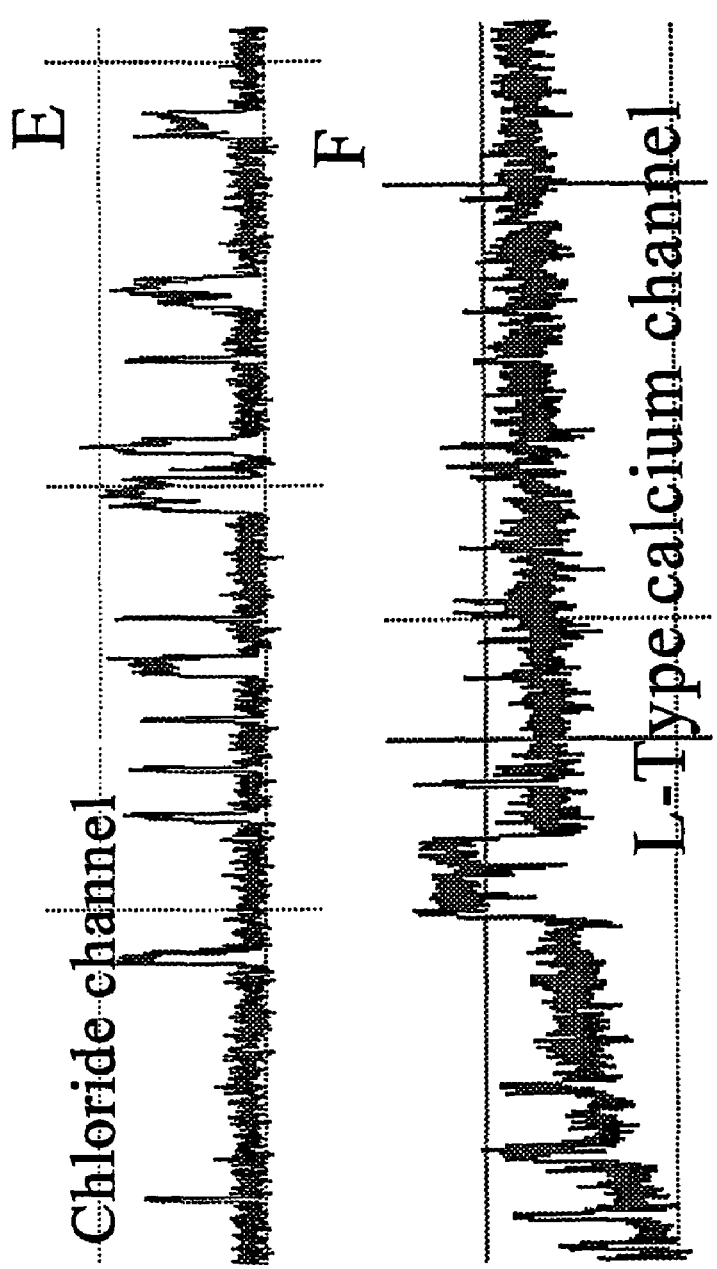
Figure 1 contd.

PATCH-CLAMPING AND ITS USE IN ANALYZING SUBCELLULAR FEATURES

FIELD OF THE INVENTION

This invention relates to patch-clamping and its use in analyzing subcellular features. In particular, it relates to a method for investigating the functional characteristics and the localisation of ion channels.

BACKGROUND OF THE INVENTION

Ion channels play a crucial role in cell function. In addition, a substantial number of studies suggests that cell specialisation is often based on the spatial distribution of these channels on the cell surface, for example in neural cells, muscle cells and epithelial cells.

Several types of ion channels have been reported to be arranged non-randomly in a specific pattern on the cell membrane, and this appears to have important functional implications. For example, it is known that voltage-gated $Na^+$ channels are densely distributed and co-localized with acetyl choline receptors in the neuromuscular junction, to enable effective chemical signal transmission. Further, NMDA receptors, which play an important role in neuronal signalling, are arranged in distinct spatial patterns, and their arrangement contributes to synaptic plasticity.

The spatial distribution of ion channels has mainly been studied by microscopy-based techniques using labelling methods. However, these studies provide practically no information on the functional characteristics of ion channels.

Patch clamping is a technique that can be used to investigate ion channel characteristics. However, it does not allow precise selection of a region of interest on a cell, and provides limited information on the important question of ion channel localization.

Scanning ion conductance microscopy (SICM) is a form of scanning probe microscopy (SPM) that allows high-resolution imaging of live cell surfaces, and of small submicrometer structures such as dendritic processes, microvilli in epithelial cells and the surface structures of cardiac myocytes. SICM has also been used in mapping exclusively ligand-sensitive ion channels such as ATP-dependent $K^+$ channels on cardiac myocytes, by combination with whole-cell patch-clamp recording (Korchev et al, Nat. Cell Biol. 2:616–619, 2000).

In SICM, a glass micropipette is typically used as a microscope probe, to scan the sample. WO-A-00/63736 discloses that SICM can be used effectively, e.g. to scan the surface of a live cell, by controlling the position of such a probe. This is achieved in response to the ion current.

SUMMARY OF THE INVENTION

According to the present invention, a method for investigating a cell comprises bringing a probe (i) close to the surface of the cell or a part thereof, at a controlled distance therefrom; and (ii) into contact with the surface, essentially normal to the surface, to achieve patch-clamping.

Apparatus according to the invention comprises the probe, means for measuring and/or controlling the distance of the probe from a surface to be scanned, means for bringing the probe into contact with the surface, and a patch-clamp amplifier. Such an amplifier is of high sensitivity, suitable for measuring current through ion channels.

In a simple embodiment of the invention, the use of optics and modulation of ion current can be used for step (i). Step (ii) involves patch-clamping, using the same probe, e.g. a micropipette or nanopipette, without the usual danger of this technique, ie. causing damage to the cell.

In a preferred embodiment, the probe is also used to scan a cell surface, i.e. by scanning probe microscopy. An image can be generated, and a part of the surface that is of interest can be identified as having a particular characteristic. Patch-clamping can then be done, very precisely, not only at that part, but then on a part of another cell having the same identified characteristic. All this can be achieved without the need for optics.

Thus, according to a preferred embodiment of the invention, the same micropipette can be used for scanning, localising, and patch clamp recording, of an ion channel of interest at a precise location on the surface of a live cell. This advanced "smart" patching can be used to map the distribution (with a spatial resolution better than 100 nm) and functional characteristics of any plasma membrane ion channel that can be detected with a patch clamp technique.

Very small cellular structures can be probed by means of the invention, including intracellular and subcellular features that cannot otherwise readily be detected. These features may be less than 1 µm, often less than 500 nm, e.g. 250 nm or below, in size.

DESCRIPTION OF PREFERRED EMBODIMENTS

The invention can combine SPM with the capability of the patch-clamping technique to investigate the functions of single ion channels. SPM preferably uses a glass micropipette as a scanning probe, and allows high-resolution imaging and micromanipulation of the sample. A suitable micropipette is described in WO-A-00/63736.

For the SPM, a suitable instrument is a scanning ion conductance microscope (SICM) that comprises the micropipette probe and a computer-controlled three-axis translation stage with measurement and feedback systems. The use of a micropipette as a SPM probe provides two distinct advantages in cell imaging and mapping of ion channels in intact cell membranes. Firstly, it provides a non-invasive scanning protocol that prevents the tip of the micropipette making direct physical contact with the specimen, by maintaining a constant distance between the probe and the sample. Secondly, it enables the direct activation and probing of single ion channels in a highly localised region (~0.01 µm$^2$) of interest on a cell surface.

The invention provides in particular a method to map ion channels on living cells. The method is based on the use of a micropipette to obtain a high resolution image of the cell's topography, using the ion conductance current for feedback. Having identified a feature of interest, the same pipette is then used to form a patch at a chosen and specific point on the cell surface. The patch can be formed in a straightforward way, since the pipette can be held at a controlled distance of, say, up to 100 nm, e.g. 25–50 nm, away from the cell surface using the ion conductance current. Simply turning off the control results in reliable formation of a giga-ohm patch. The fact that the pipette can be held normal to the cell surface contributes to this reliability, in contrast to a conventional patch clamp where the pipette is at an angle.

The invention allows investigation of very small structures. In cells, such features are known, and include plasma membrane, golgi, endoplasmic reticulum, nuclear envelope, sub-micron dendrites in neural cells, microvilli (0.1–1.0 µm) in epithelial cells, the inside of T-tubules (~250 nm diameter) of muscle cells and other remote positions on cell surfaces, e.g. the leading edge of a migrating cell. Further, the invention enables the study of ion channels, not only in small cells such as sperm, but in sub-micrometer cellular structures.

More particularly, the invention allows the investigation of evaginations of cell membranes such as dendrites, microvilli and pseudopodia "hair-like" extrusions; invaginations of cell membranes such as caveoli, t-tubules, grooves, clefts and vescicles (pinocytotic); intercellular membranes such as postsynaptic membranes, neuromuscular junctions, gap junctions and membranes apposing intercellular spaces; subcellular organelles such as mitochondria, sarcoplasmic reticulum and chloroplasts; and small cells such as platelets, sperm cells, bacteria and erythrocytes.

The sample under investigation may be in culture or isolated cells. In fact, isolation is not essential. The sample may be a whole body part, e.g. a blood vessel. Alternatively, it may be a slice of tissue, e.g. of brain. No further preparation may be required.

The cells under investigation may be bacteria, plant or animal cells. In certain cases, the probe may be used to deliver a substance to a cell, so that intracellular components can be investigated without breaking the structure.

The method of the invention has general applicability for the mapping of ion channels as well as a robust and reliable method to perform patch clamping. It also has other applications. For example, it can be used to relate the cell topography to the location of other molecular structures, for example, by labelling these structures with green fluorescent protein (GFP) or antibodies. This is because the micropipette can be used for the local delivery of biologically active substances to a specified area of the cell surface. The technique may also be adapted to map the localisation of ligand-regulated, mechano-sensitive or voltage-gated ion channels, since the micropipette probe can be used to deliver defined chemical, electrical or mechanical stimuli to the localised regions of the cell surface during the scan. The technique may also have general applications in the investigation of ion channel functional localisation in intact cell membranes of different cell types.

In cardiac myocytes, as in most excitable cells, action potential propagation depends essentially on the properties of ion channels that are functionally and spatially coupled. By means of the invention, it has been found that the L-type calcium and chloride channels are distributed and co-localized in the region of T-tubule openings, but not in other regions of the myocyte. In addition, chloride channels were found in narrowly defined regions of Z-grooves. This suggests a new synergism between these types of channels that may be relevant for action potential propagation along the T-tubule system and excitation-contraction coupling, and is evidence of the invention's value.

The ability to investigate ion channels makes the invention of value in screening potential therapeutic agents for their ability to block or otherwise act on such channels, e.g. Na, K, Ca or Cl ion-channels, and ligand-gated receptors coupled thereto. Such screening can generally be conducted by known means, e.g. by conducting a series of experiments on various potential agents with respect to a control or predetermined value.

Figure 2:
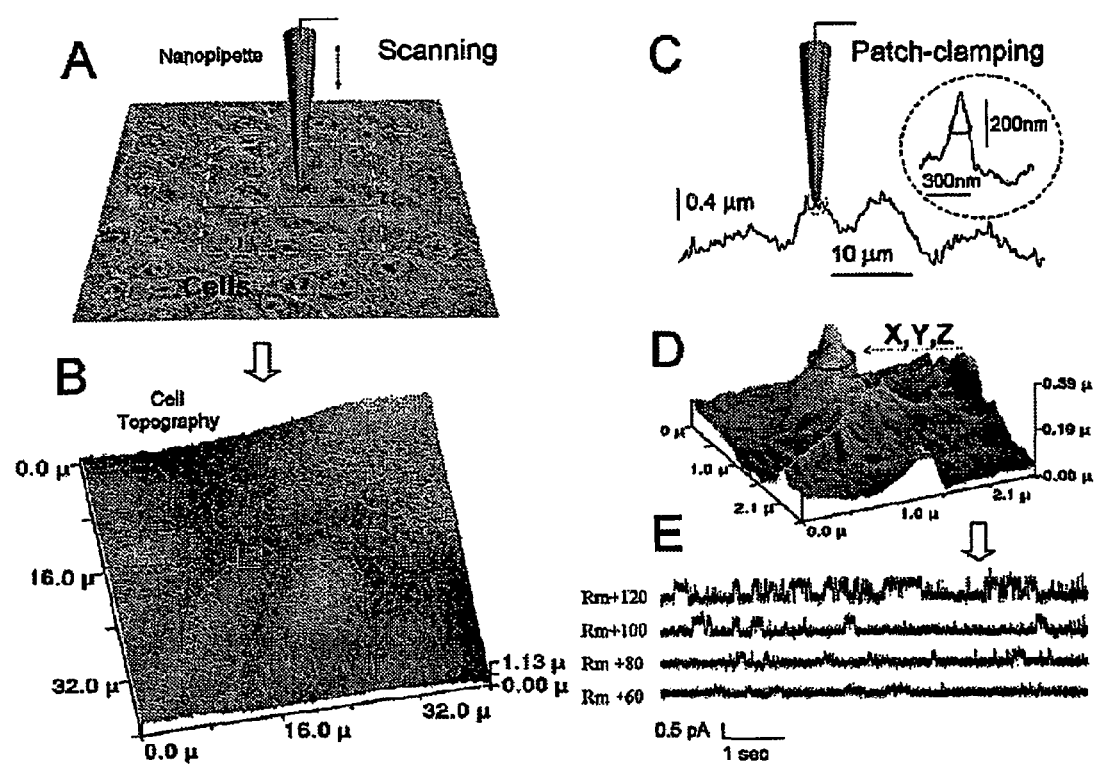

The invention will now be described by way of example only with reference to the accompanying drawings, in which:

FIG. 1 (panels A to F) is a schematic view of a device that can be used to practise the invention, and also shows results; and FIGS. 2 (panels A to E), 3 (panels A to F) and 4 (panels A to E) are views and results analogous to those in FIG. 1, and more particularly described in the Examples.

FIG. 1 demonstrates the capability of extremely high resolution and precise selection of a particular area of a heart cell surface, and patch-clamping it. Panel A is a diagram of the experimental set-up. The same micropipette serves firstly as the scanning probe and then as the pipette for patch clamp. The pipette rasters across the surface to build up a topographic image, maintaining a fixed distance from the surface of the cell. The cell surface is irregular, and the feedback system based on the ion current is used to keep the distance between the tip of the probe and the cell surface constant during the scan. The irregular surface means that the probe has to move up and down in the vertical Z direction. Feeding the XYZ coordinates into a suitably programmed computer generates an image of the heart cell surface; this image is shown in panel B. Knowing the coordinates in the image allows selection of an area of interest, and as indicated in panel C. Next, the control is turned off and the probe then forms a patch to the cell surface at the selected area. The area visualised in the image, as shown in panel D, is the mouth of a T tubule; this is shown as a dark indentation on the image. The electrophysiological records obtained from the patch placed in this particular selected area are illustrated in panels E (chloride channel) and F (L-type calcium channel).

The following Examples illustrate the invention, with reference to FIGS. 2–4 which will now be described in greater detail.

FIG. 2: (A) In order to perform patch-clamp recording from a selected nanostructure on the cell membrane, which is not discernible under the light microscope, an area of interest on an A6 kidney epithelial cell monolayer is selected (white dotted square). The patch-clamp nanopipette (tip radius ~100 nm), with a backfill solution for investigating a specific ion channel, is mounted on an X-Y-Z piezo stage and is used to image the cell surface topography (B) controlled by SICM. The ion current for SICM feedback control is measured through a standard patch-clamp amplifier. (B) The topographic image provides detailed three-dimensional information of the living cell's surface. Pronounced microvilli and raised cell borders are visible on the surface, that are normally only visible by SEM of fixed cells. (C) For ion channel recording, the nanopipette was placed over a selected microvillus indicated by the pipette on the height profile across the cell monolayer. The profile was derived from the image indicated by the dashed line on panel B. The inset figure represents a more detailed profile of the selected microvillus. (D) A further scan with higher resolution is performed to position the nanopipette exactly on the tip of the microvillus. The image represents the topography of the selected microvillus. After completion of the scan, the pipette is lowered down vertically onto the apex of the microvillus (red circle). Light suction is applied to the nanopipette, which results in the formation of a GΩ seal. Thus the nanopipette is now used for patch-clamp recording. (E) Cl⁻ channel currents were recorded at the top of a microvillus in cell-attached configuration.

Figure 3:
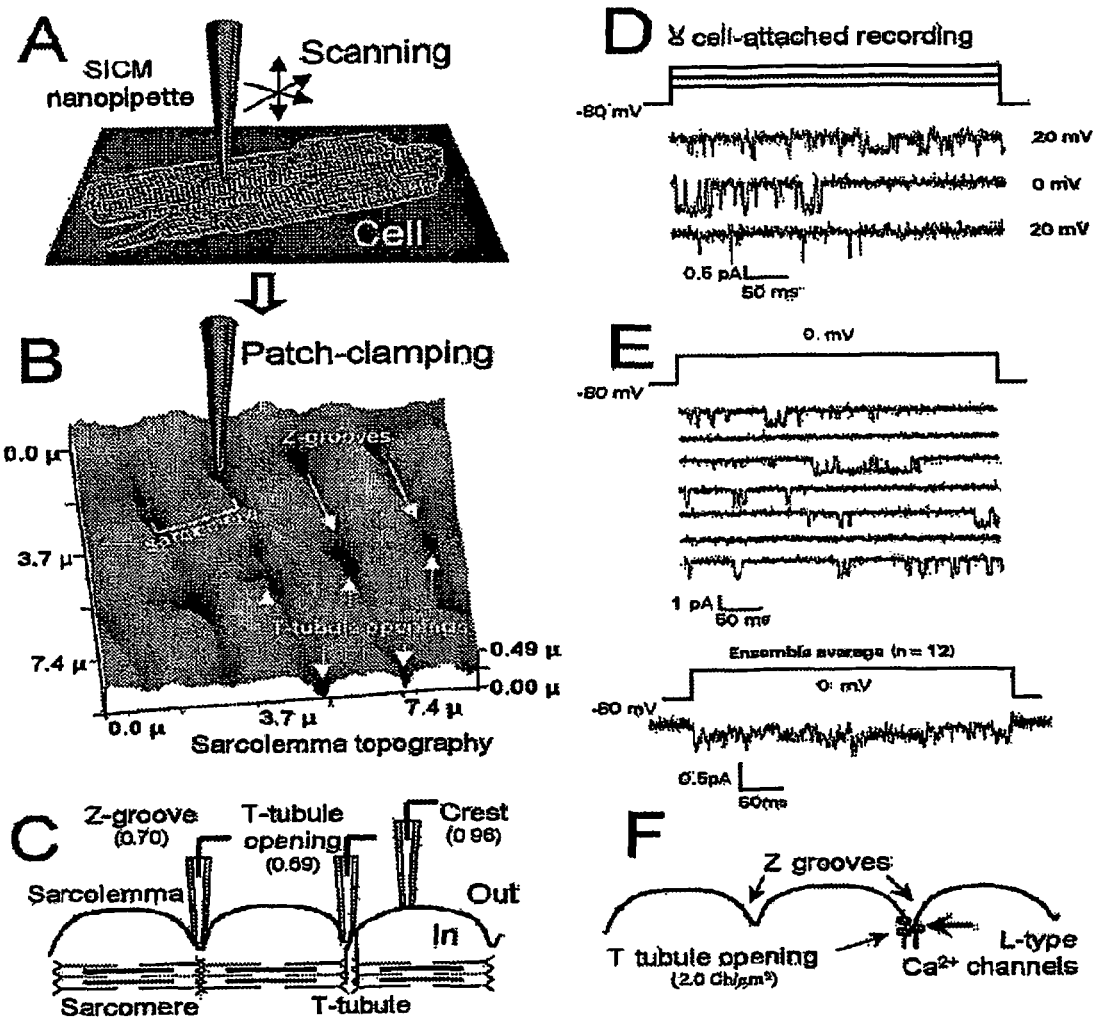

FIG. 3: (A) In order to perform patch-clamp recording from different regions on the cardiac myocyte sarcolemma, an area of interest is selected (white dotted square). The patch-clamp nanopipette with a backfill solution for investigating $Ca^{2+}$ channels is used to image the cell surface topography controlled by SICM. (B) Experimental topographic image of a representative rat cardiomyocyte membrane. Z-grooves, T-tubule opening and characteristic sarcomere units are marked. (C) Functional schematic of sarcomere units showing the position of the probed region (Z-groove, T-tubule opening and scallop crest). Probabilities of forming a GΩ seal as a function of surface position are shown in parenthesis. (D) Cell-attached $Ba^{2+}$ current transients at voltages of +20, 0, −20 mV. (E) Several current transients elicited at 0 mV from one patch and ensemble average of 12 transients showing typical L-type inactivation kinetics. (F) Statistical distribution of L-type $Ca^{2+}$ channels with the highest density near the T-tubule opening.

Figure 4:
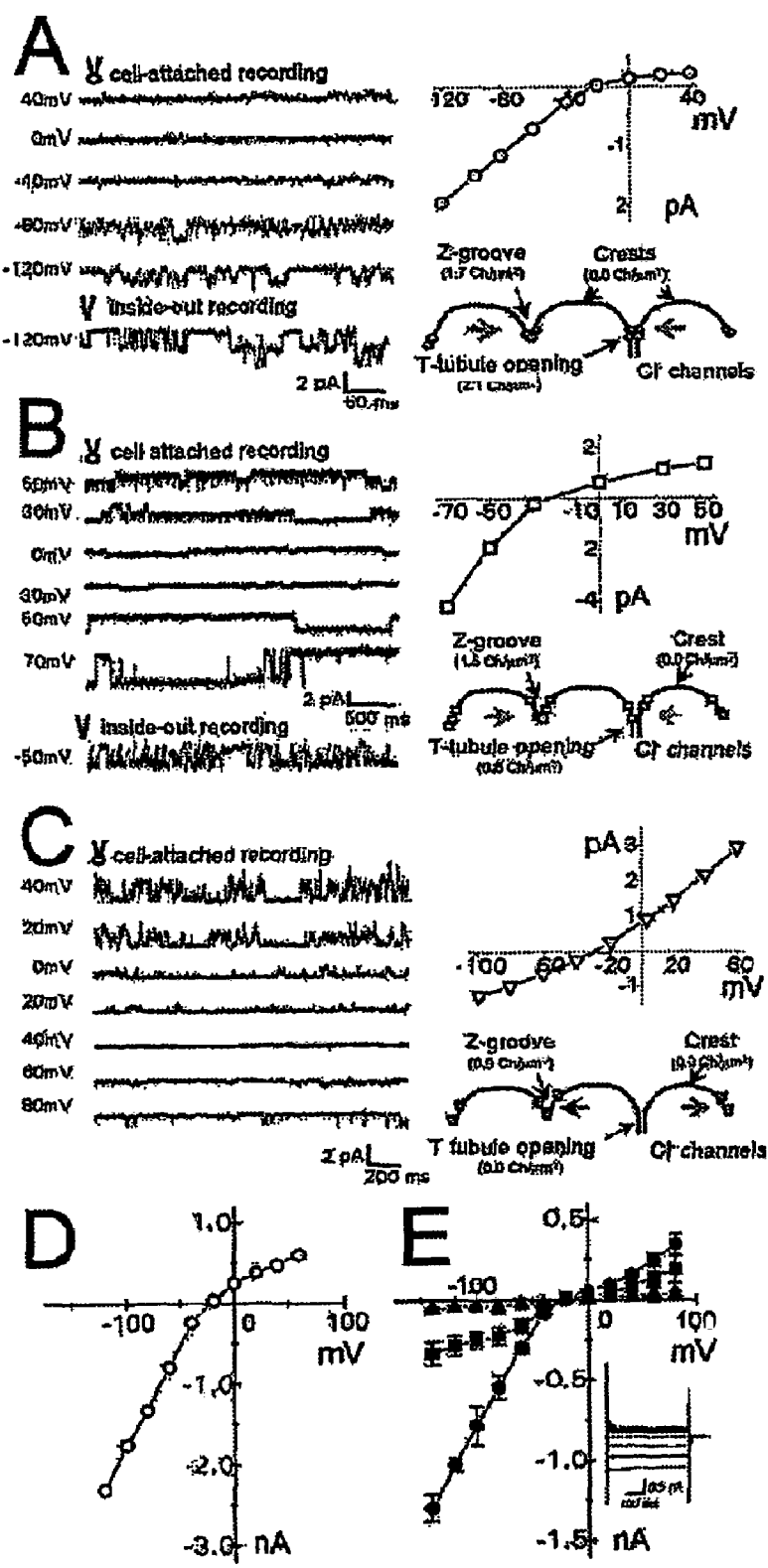

FIG. 4: Channels with 3 different current types were found. (A) A small-conductance inwardly rectifying channel ($Cl_{SIR}$). (B) A large-conductance inwardly rectifying channel ($Cl_{LIR}$). (C) An outwardly rectifying channel ($Cl_{OR}$). For each type of channel, a family of currents at different voltages (on the left side of the panels), current-voltage characteristics (on the top right side of the panels) and channel densities at different surface positions (on the bottom right side of the panels) are shown. The mean reversal potential was −31.2±2.4 mV (n=5) for (A)−31.8±3.4 mV (n=5) for (B) and −33.5±3.0 mV (n=4) for (C). (D) Calculated whole-cell current extrapolated from single-channel currents. (E) Current-voltage characteristics of experimental whole-cell currents obtained from 22 cells (black circles). Currents were partially blocked by 300 μM of the $Cl^-$ channel antagonist stilbene disulfonate (SITS) (black squares) (n=12) and almost completely blocked by 1 mM $Cd^{2+}$ (black triangles) (n=5). Currents were measured at plateau level. The inset figure shows a typical family of whole-cell currents.

EXAMPLE 1

Epithelial Kidney Cells:

A single A6 cell line was kindly provided by Dr DeSmet. All experiments were carried out between 127–134 passages. Cells were cultured as described previously (Sariban-Sohraby et al, J. Biol. Chem. 259:11221–11225, 1984) on glass cover slips. Cells were grown and kept in a 1:1 mixture of modified Ham's F-12 medium and Leibovitz's L-15 medium, modified to contain 105 mM NaCl and 25 mM $NaHCO_3$. The mixture was supplemented with 10% fetal calf serum, 200 μg/ml streptomycin and 200 units/ml penicillin. Cells were maintained at 28° C. in an atmosphere of humidified air plus 1% $CO_2$. Cells were passaged and used between days 4 and 5 when they were 90–95% confluent. Aldosterone was added in a concentration of 1.5 μM 48 hours before the experiments. Single channel recordings were performed using a bath solution and pipette backfill solution both composed of (in mM) NaCl 140, KCl 5, $MgCl_2$ 0.8, $CaCl_2$ 1.2 and HEPES 10 (pH=7.4).

Imaging:

Topographic imaging of the cell was performed using previously described scanning ion conductance microscopy (SICM) methods (Korchev et al, Biophys J. 73:653–658, 1997). Briefly, a pipette mounted on a piezo stage is moved over the cell while maintaining a fixed distance to the surface. This is achieved by a feedback control keeping the ion current through the pipette constant. The set-up was adapted for high-resolution patch-clamping by replacing the current amplifier with a commercial patch-clamp amplifier (Axopatch 200B, Axon Instruments, Foster City, Calif.). Nanopipettes were made from 1.00 mm outer diameter and 0.58 mm inner diameter borosilicate glass capillaries (Intracel, Herts, England) using a laser-based puller (P-2000, Sutter Instrument Co., San Rafael, Calif.). Pipettes were used without any further treatment such as fire polishing or sylgard shielding. The pipette tip radius determined by scanning electron microscopy was about 100 nm.

Validation:

Reproducibility of precise pipette positioning was verified by repeating surface scans of the same area several times. During this period, no shift between individual scan images was observed.

FIG. 2 shows patch-clamping of cellular structures with very small dimensions such as microvilli, which are invisible under a light microscope (FIG. 2A). Patch-clamping of these structures has not been possible before. A topographic image of epithelial kidney cells was obtained (FIG. 2B). To locate the pipette precisely over a small feature of the cell, subsequent scans with higher resolution (FIG. 2D) were performed. A GΩ seal was formed at the very tip of a microvillus (FIG. 2C). Subsequently, ion currents were studied in cell-attached configuration (FIG. 2E). In most cases, inside-out recording was performed after cell-attached recording in order to confirm the nature of the observed channels.

Other examples of cellular structures of small size are neuronal dendrites and sperm cells. Their dimensions have previously rendered direct electrophysiological recordings unfeasible. The novel scanning patch-clamp technique has been applied to hippocampal neurons and superior cervical ganglion cells. It was found that $K^+$ and $Ca^{2+}$ channel currents can be measured on very fine dendrites ranging from 100 to 200 nm. Using scanning patch-clamp, high success rates were achieved for cell-attached recording on sea-urchin sperm cells and on human sperm cells, demonstrating an abundance of $Ca^{2+}$ and $Cl^-$ channels on the cell body.

Since the patch is performed by an orthogonal approach, controlling the pipette's distance electro-mechanically, this method is more reliable than conventional patch-clamping, and less prone to variation between experimenters. The probability of obtaining a seal was 0.70 at the regions of the Z-groove, 0.59 at the T-tubule opening and 0.96 at the scallop crest. The high success rate for obtaining patches allowed the efficient accumulation of data points and statistical averaging of the channel distribution at distinct locations on the cell surface.

EXAMPLE 2

Cardiac Myocytes:

Left ventricle cells from the rat myocardium were isolated as previously described (Harding et al, J. Mol. Cell Cardiol. 20:635–647, 1988). Cells were allowed to attach to polystyrene cell culture dishes filled with bath solutions.

$Ca^{2+}$ Channel Experiments:

the bath solution was composed of (in mM) K-glutamate 120, KCl 25, $MgCl_2$ 2, $CaCl_2$ 1, EGTA 2, glucose 10 and HEPES 10, adjusted to pH 7.4 with NaOH. Pipette backfill solution contained (in mM) $BaCl_2$ 70, HEPES 10 and sucrose 110, adjusted to pH 7.4 with tetraethylammonium-OH (TEA-OH). Experiments were started after cells had ceased to contract due to depolarization by high [$K^+$] in the bath solution.

Cell-Attached $Cl^-$ Current Experiments:

the bath solution contained (in mM) K-glutamate 120, KCl 25, $MgCl_2$ 2, $CaCl_2$ 1, EGTA 2, glucose 10 and HEPES 10, adjusted to pH 7.4 with CsOH. The pipette backfill solution contained N-methyl-D-glucamine-Cl (NMDG-Cl)

108, HEPES 5, glucose 5.5 and EGTA 1, adjusted to pH 7.4 with TEA-OH. For whole-cell Cl⁻ current experiments, the bath solution was composed of (in mM) NaCl 100, $MgCl_2$ 1, $CaCl_2$ 1, $BaCl_2$ 2, $NaH_2PO_4$ 0.33, HEPES 10 and glucose 10, adjusted to pH 7.4 with TEA-OH (total $[Cl^-]_o$ 108 mM). To prevent contamination from $Ca^{2+}$ currents, 30 μM nifedipine was always present in the bath. The pipette backfill solution contained (in mM) CsCl 30, $MgCl_2$ 1, HEPES 10, EGTA 5 and $Cs_2SO_4$ 70, adjusted to pH 7.4 with CsOH. Considering an estimated $[Cl^-]_i$ of 32 mM (25), the $[Cl^-]_i/[Cl^-]_o$ ratio was thereby similar in cell-attached and whole-cell conditions.

Results:

An objective of these procedures was to determine the functional localization of calcium and chloride channels in the cardiac myocyte sarcolemma. As described in greater detail below, it was found that L-type $Ca^{2+}$ channels are located in the T-tubule region of the cardiac myocyte sarcolemma. It was also found that three types of Cl⁻ channels are located in the regions of T-tubule openings and Z-grooves.

The distribution of L-type $Ca^{2+}$ channels in rat cardiac myocytes was identified and mapped. FIG. 3B shows a representative topographic image of the cell surface. The sarcomeres, openings of transverse tubules (T-tubules) and Z-grooves can be easily identified. A total of 233 patches were performed, equally probing three different regions of the cardiomyocyte sarcolemma; the T-tubule openings, Z-grooves and scallop crests (FIG. 3C). Ion currents in cell-attached configuration were only detected when the pipette was located in the T-tubule opening. Current traces shown in FIG. 3D and current-voltage curves (not shown) are characteristic of L-type $Ca^{2+}$ channels, which have been described previously in rat ventricular myocytes (Premkurmar, Mol. Pharmacol. 56:1138–1142, 1999). Several single-channel $Ca^{2+}$ currents of one patch are shown in FIG. 3E, as well as the ensemble average, which identifies them as L-type. T-tubule openings vertically by lowering the pipette tip 0.3–2.0 μm deep into the cell using a vertical SICM piezo stage. One out of every eight patches in the T-tubule openings exhibited L-type $Ca^{2+}$ currents, and these were not found in any other probed regions of the cell (FIG. 3F). Other studies suggest that L-type $Ca^{2+}$ channels are mainly distributed in the membrane of the T-tubule system. Using the probability of obtaining a patch containing calcium channels (p=0.125) and estimating the membrane patch area (0.06 μm²), based on the pipette geometry and supposing a hemispherical shape of the membrane patch, the density of L-type $Ca^{2+}$ channels at T-tubule openings was estimated to be approximately 2 channels/μm². Similar densities have been found in guinea pig cardiomyocytes using immunogold-labelling.

Three types of Cl⁻ currents were distinguished on the basis of single-channel conductance and rectification in cell-attached mode (FIG. 4). Channels were identified as being Cl⁻ conductive from the reversal potential of the single-channel current-voltage relations. It was also taken into account that any K⁺ currents were blocked by TEA, and impermeable NMDG⁺ was the only cation present in the pipette. Two current types exhibited similar inward rectification and remained active after pulling the pipette off the cell to obtain the inside-out configuration. Channels of these subtypes may belong to the ClC family since their current-voltage characteristics resembled those of ClC channels in other tissue or types of cardiomyocytes. Expression of ClC-2 and ClC-3 channels in rat ventricle cells has previously been demonstrated, but the lack of information on ion current characteristics in rat cardiac myocytes did not allow definitive identification before. Typically for Cl⁻ channels, clearly distinguishable current substrates were observed (see FIG. 4A, bottom trace, FIG. 4B, top trace). A third type of current was found to be outwardly rectifying (FIG. 4C) and resembled currents that have been previously described in rabbit cardiomyocytes using conventional patch-clamp techniques. A total of 305 patches were performed at three distinct positions on the cell surface; the scallop crest, Z-groove and T-tubule opening. All three types of Cl⁻ channels are only distributed in the regions of Z-grooves and around the T-tubule openings, but not on the scallop crest (FIG. 4).

In summary, the invention allows the high-resolution localisation of single ion channels on a living cell surface. The "smart" patch technique produces topographical images of about 100 nm resolution and enables patch-clamp recording from very small cellular structures that are invisible under the light microscope. It can be used on any functional ion channel without the need to know the molecular identity of the examined channel proteins. In contrast, conventional antibody staining techniques often require cells to be fixed and do not provide functional characteristics of the obtained ion channel distribution. The technique can be applied to small cellular structures where patch-clamping has been difficult or impossible to perform so far and may be used in a wide range of cell types such as muscle cells, epithelial cells, neurons and sperm cells. In addition, it is a robust and reliable method to perform patch-clamping. Potential applications of the technique also include the mapping of ligand-gated or mechano-sensitive ion channels, as the nanopipette can be used to deliver defined chemical, electrical or mechanical stimuli to narrowly defined areas on the cell surface.

The invention claimed is:

1. A method for investigating a cell, which comprises using scanning ion conductance microscopy and bringing a probe close to the surface of the cell or a part thereof, and maintaining the probe at a fixed distance from the surface of the cell or part thereof using feedback control based on modulated ion current; and bringing the probe into contact with the surface, essentially normal to the surface, of the cell to achieve patch-clamping.

2. The method according to claim 1, which additionally comprises identifying the part of the cell by mapping the surface of the cell with the probe.

3. The method according to claim 2, which is repeated on another cell, at a part of the surface of the other cell having the same identifying characteristic.

4. The method according to claim 1, wherein the cell or the part thereof is less than 1 μm in size.

5. The method according to claim 4, wherein the cell or the part thereof is a whole cell, a subcellular feature or intracellular body.

6. The method according to claim 1, wherein the cell or part thereof is less than 100 nm in size.

7. The method according to claim 6, wherein the cell or the part thereof is a whole cell, a subcellular feature or intracellular body.

8. The method according to claim 1, wherein the probe is a micropipette or nanopipette.

9. A method for determining whether a compound is a potential therapeutic agent, which comprises determining the effect of the compound on a cell surface identified by a method according to claim 1.

10. The method according to claim 9, wherein the effect is with respect to an ion channel.

11. An apparatus which comprises a probe; means for maintaining the probe at a fixed distance from the surface of an object using feedback control based on modulated ion current; means for bringing the probe into contact with the surface; and a patch-clamp amplifier.

12. The apparatus according to claim 11, which additionally comprises a device for scanning probe microscopy.

13. The apparatus according to claim 12, which additionally comprises means for imaging the surface.

14. An apparatus which comprises a scanning ion conductance microscope and a patch-clamp amplifier, wherein said scanning ion conductance microscope comprises:

a probe;

a means for measuring or controlling the distance of the probe from the surface of an object, using feedback control based on modulated ion current, to maintain the probe at a fixed distance from the surface of the object; and a means for bringing the probe into contact with the surface of the object so as to achieve patch-clamping.

15. The apparatus according to claim 14, which additionally comprises means for imaging the surface.

* * * * *